(12) United States Patent
Hansen et al.

(10) Patent No.: US 11,615,178 B2
(45) Date of Patent: *Mar. 28, 2023

(54) SYSTEMS AND METHODS FOR SECURING OPERATION OF AN ULTRASOUND SCANNER

(71) Applicant: Clarius Mobile Health Corp., Vancouver (CA)

(72) Inventors: Trevor Stephen Hansen, Vancouver (CA); Benjamin Eric Kerby, Richmond (CA); Kris Dickie, Vancouver (CA); Jing Cheng, Burnaby (CA)

(73) Assignee: Clarius Mobile Health Corp., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/209,185

(22) Filed: Mar. 22, 2021

(65) Prior Publication Data

US 2021/0209212 A1     Jul. 8, 2021

Related U.S. Application Data

(63) Continuation of application No. 15/786,279, filed on Oct. 17, 2017, now Pat. No. 10,956,551.
(Continued)

(51) Int. Cl.
*G06F 21/33* (2013.01)
*A61B 8/00* (2006.01)
*G06F 21/44* (2013.01)

(52) U.S. Cl.
CPC .......... *G06F 21/335* (2013.01); *A61B 8/4438* (2013.01); *A61B 8/465* (2013.01);
(Continued)

(58) Field of Classification Search
CPC ... H04L 67/12; H04L 63/105; H04L 2209/38; H04L 9/3247; H04L 9/3263; G06F 21/31;
(Continued)

(56) References Cited

U.S. PATENT DOCUMENTS 6,129,671 A     10/2000  Hastings
7,953,671 B2 *   5/2011  Bishop ............... G06Q 20/3674
                                                    705/76
(Continued)

FOREIGN PATENT DOCUMENTS

EP            1244994 B1      7/2004

OTHER PUBLICATIONS

Q.-H. Huang, Z. Yang, W. Hu, L.-W. Jin, G. Wei and X. Li, "Linear Tracking for 3-D Medical Ultrasound Imaging," in IEEE Transactions on Cybernetics, vol. 43, No. 6, pp. 1747-1754, Dec. 2013, doi: 10.1109/TSMCC.2012.2229270. (Year: 2013).*

*Primary Examiner* — Khalid M Almaghayreh
(74) *Attorney, Agent, or Firm* — Julian Ho; Susan Ben-Oliel

(57) ABSTRACT

The present embodiments relate generally to systems and methods for securing operation of an ultrasound scanner for use with a multi-use electronic display device. In some embodiments, the multi-use electronic display device can control whether the ultrasound scanner is permitted to generate ultrasound image data for display based on an institution affiliation status of the ultrasound scanner retrieved from a server. In some embodiments, the multi-use electronic display device can control whether the ultrasound scanner is permitted to generate ultrasound image data for display based on whether a digital certificate provided by a server is successfully validated.

19 Claims, 9 Drawing Sheets

Related U.S. Application Data

(60) Provisional application No. 62/542,256, filed on Aug. 7, 2017.

(52) U.S. Cl.
CPC .............. *A61B 8/467* (2013.01); *A61B 8/565* (2013.01); *G06F 21/44* (2013.01); *A61B 8/4427* (2013.01); *A61B 8/4472* (2013.01); *G06F 2221/2151* (2013.01)

(58) Field of Classification Search
CPC .................. G06F 21/335; G06F 21/44; G06F 2221/2151; A61B 8/4438; A61B 8/465; A61B 8/467; A61B 8/565; A61B 8/4427; A61B 8/4472
See application file for complete search history.

(56) References Cited

U.S. PATENT DOCUMENTS

| | | | | |
|---|---|---|---|---|
| 8,396,802 | B2 * | 3/2013 | Dala | H04L 63/0428 380/231 |
| 10,140,421 | B1 * | 11/2018 | Bernard | G06V 10/764 |
| 10,956,551 | B2 | 3/2021 | Hansen et al. | |
| 2004/0210755 | A1 * | 10/2004 | Becker | G06F 21/6218 713/167 |
| 2007/0016783 | A1 * | 1/2007 | Saito | H04L 9/3247 713/175 |
| 2007/0080223 | A1 | 4/2007 | Japuntich | |
| 2008/0232367 | A1 * | 9/2008 | Thomas | H04L 12/1868 370/390 |
| 2011/0119075 | A1 * | 5/2011 | Dhoble | G16H 10/60 705/2 |
| 2012/0136923 | A1 * | 5/2012 | Grube | G06Q 10/06315 709/203 |
| 2012/0271655 | A1 * | 10/2012 | Knobel | G06Q 30/02 705/3 |
| 2013/0111353 | A1 * | 5/2013 | Ueda | G06F 3/04817 709/219 |
| 2013/0190624 | A1 * | 7/2013 | Beger | A61B 8/4245 600/443 |
| 2013/0208955 | A1 * | 8/2013 | Zhao | G16Z 99/00 382/128 |
| 2013/0331675 | A1 * | 12/2013 | Batman | G01N 33/48785 600/365 |
| 2014/0063219 | A1 | 3/2014 | Stonefield et al. | |
| 2014/0142984 | A1 * | 5/2014 | Wright | G06Q 40/08 705/3 |
| 2014/0338663 | A1 | 11/2014 | Pirzada | |
| 2015/0101066 | A1 * | 4/2015 | Fram | G06F 21/6245 726/28 |
| 2015/0245816 | A1 * | 9/2015 | Poland | A61B 8/14 600/447 |
| 2015/0278444 | A1 * | 10/2015 | Westin | G16H 30/20 382/128 |
| 2015/0304736 | A1 * | 10/2015 | Lal | G06F 21/72 380/210 |
| 2015/0317466 | A1 * | 11/2015 | Kumar | H04L 63/0861 726/7 |
| 2016/0027399 | A1 * | 1/2016 | Wilde | G09G 5/003 345/520 |
| 2016/0100824 | A1 * | 4/2016 | Kim | A61B 8/461 600/437 |
| 2017/0063931 | A1 * | 3/2017 | Seed | H04L 67/12 |
| 2017/0068792 | A1 * | 3/2017 | Reiner | A61B 17/1214 |
| 2017/0086787 | A1 * | 3/2017 | Sun | A61B 8/467 |
| 2017/0091400 | A1 * | 3/2017 | Richards | G06F 21/6263 |
| 2017/0140145 | A1 * | 5/2017 | Shah | G16H 80/00 |
| 2017/0235880 | A1 * | 8/2017 | Wright | G06Q 10/10 705/2 |
| 2017/0249424 | A1 * | 8/2017 | Augusto Di Grandi Nery | G16H 40/67 |
| 2018/0121610 | A1 * | 5/2018 | Cayle | G16H 40/20 |
| 2018/0359102 | A1 * | 12/2018 | Kakutani | H04L 63/0823 |
| 2018/0360410 | A1 * | 12/2018 | Sun | G16H 30/20 |
| 2019/0199666 | A1 * | 6/2019 | Pattan | H04L 12/1895 |
| 2019/0220174 | A1 * | 7/2019 | Rana | G06F 21/31 |
| 2019/0350563 | A1 * | 11/2019 | Omero | H04N 21/2187 |
| 2020/0128401 | A1 * | 4/2020 | Shin | H04W 12/61 |
| 2021/0286868 | A1 * | 9/2021 | Kragh | H04L 63/0823 |

* cited by examiner

SYSTEMS AND METHODS FOR SECURING OPERATION OF AN ULTRASOUND SCANNER

CROSS-REFERENCE TO RELATED APPLICATIONS

This application is a continuation of U.S. patent application Ser. No. 15/786,279 entitled "SYSTEMS AND METHODS FOR SECURING OPERATION OF AN ULTRASOUND SCANNER" filed on Oct. 17, 2017, which claims the benefit of U.S. Provisional Patent Application No. 62/542,256 entitled "SYSTEMS AND METHODS FOR SECURING OPERATION OF AN ULTRASOUND SCANNER" filed on Aug. 7, 2017, each of which is incorporated by reference herein in its entirety.

FIELD

The present disclosure relates generally to ultrasound imaging, and in particular, systems and methods of securing operation of an ultrasound scanner that may be used with a multi-use electronic display device.

BACKGROUND

Ultrasound imaging systems typically include several components: a transducer that sends and receives ultrasound signals; electronics capable of processing ultrasound image data from the transducer; and a display for displaying ultrasound images. These various components have traditionally been provided by a single ultrasound manufacturer. When a single manufacturer provides the various components of the ultrasound imaging system, it may be easier to secure operation of the ultrasound imaging system. For example, they can design hardware interfaces between the various components to ensure that only compatible components are used with each other.

Some modern portable ultrasound manufacturers provide hardware for only certain components of an ultrasound imaging system. For example, it is possible to provide an ultrasound scanner that incorporates the ultrasound transducer and some of the electronics for generating ultrasound image data. These ultrasound scanners may connect to multi-use electronic display devices (such as a tablet computer) for display of generated ultrasound image data.

It may be difficult to secure the operation of an ultrasound scanner in these portable ultrasound systems. For example, since a manufacturer does not have control over the physical characteristics of the display device, it may be difficult to use hardware interfaces to provide security. Also, unlike processing and display devices supplied directly by a manufacturer, multi-use electronic display devices are not within the strict control of the manufacturer. This may increase the possibility of malicious or incompatible software being loaded onto the multi-use electronic display devices. Such software may attempt to use a given ultrasound scanner without authorization.

Moreover, since the portable ultrasound scanners are typically smaller in physical size and weight, they may potentially be more easily lost or stolen. This may further increase the possibility that unauthorized individuals may attempt to use a given ultrasound scanner.

There is thus a need for improved ultrasound systems and methods that secure operation of an ultrasound scanner. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION

Figure 1:
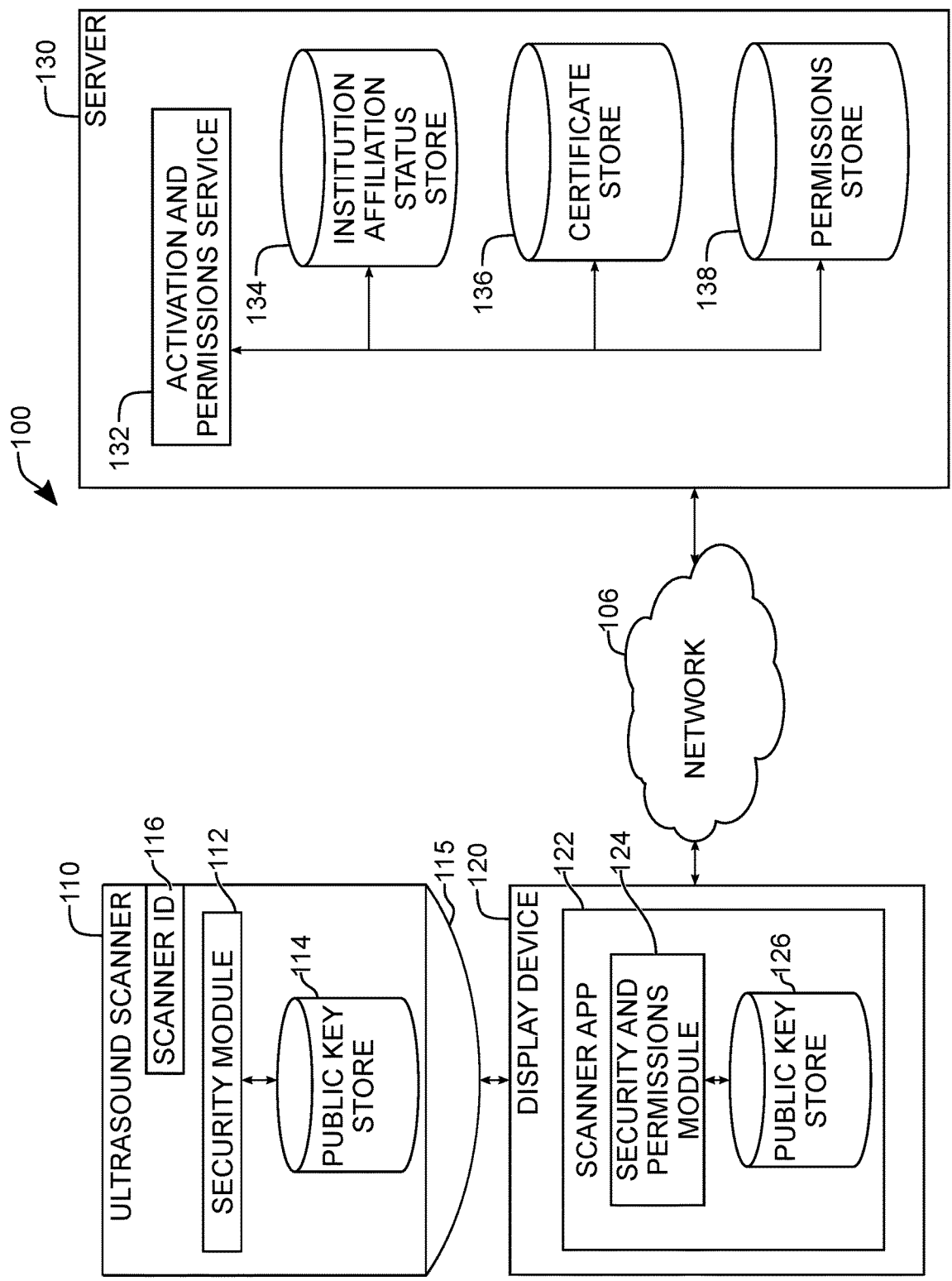
FIG. 1 shows a block diagram of a system for securing operation of an ultrasound scanner, in accordance with at least one embodiment of the present invention.

In a first broad aspect of the present disclosure, there is provided a method of controlling operation of an ultrasound scanner by a multi-use electronic display device, the method involving: determining availability of the ultrasound scanner for connecting to the multi-use electronic display device; retrieving a scanner identifier from the ultrasound scanner; sending the scanner identifier to a server for determining an institution affiliation status of the ultrasound scanner; receiving the institution affiliation status of the ultrasound scanner; based on the institution affiliation status, controlling whether the ultrasound scanner is permitted to generate ultrasound image data for display on the multi-use electronic display device.

In some embodiments, the multi-use electronic display device is not associated with an institution account, and prior to the controlling, displaying a user interface for receiving input to select the institution account to be associated with the multi-use electronic display device.

In some embodiments, the multi-use electronic display device is associated with an institution account.

In some embodiments, the institution affiliation status indicates the ultrasound scanner is affiliated with the institution account, and the ultrasound scanner is permitted to generate ultrasound image data for display on the multi-use electronic display device.

In some embodiments, the institution affiliation status indicates the ultrasound scanner is affiliated with another institution account different from the institution account associated with the multi-use electronic display device, and the ultrasound scanner is prevented from generating ultrasound image data for display on the multi-use electronic display device.

In some embodiments, the institution affiliation status indicates the ultrasound scanner is unaffiliated, and the method further involves: transmitting a request to the server to link the ultrasound scanner to the institution account associated with the multi-use electronic display device, wherein the server updates the institution affiliation status of the ultrasound scanner to indicate the ultrasound scanner is affiliated with the institution account; receiving confirmation that the server has updated the institution affiliation status of the ultrasound scanner; and permitting the ultrasound scanner to generate ultrasound image data for display on the multi-use electronic display device.

In some embodiments, the association between the institution account and the multi-use electronic display device is provided by a user account logged into an application executing on the multi-use electronic display device, the application configured for communicating with the ultrasound scanner.

In some embodiments, prior to controlling whether the ultrasound scanner is permitted to generate ultrasound image data, the method further involves: receiving a digital certificate from the server; and forwarding the digital certificate to the ultrasound scanner, wherein the ultrasound scanner attempts to validate the received digital certificate; wherein the controlling whether the ultrasound scanner is permitted to generate ultrasound image data for display on the multi-use electronic display device is further based on whether the ultrasound scanner successfully validates the received digital certificate.

In some embodiments, the multi-use electronic display attempts to validate the digital certificate, and the controlling whether the ultrasound scanner is permitted to generate ultrasound image data for display on the multi-use electronic display device is further based on whether the multi-use electronic display device successfully validates the received digital certificate.

In some embodiments, the multi-use electronic display device is provided with a public key, and the attempting to validate the digital certificate involves determining whether the digital certificate was digitally signed with a private key corresponding to the public key.

In some embodiments, the digital certificate includes an approved scanner identifier, and the method further involves: determining whether the approved scanner identifier matches the scanner identifier retrieved from the ultrasound scanner; and wherein the controlling whether the ultrasound scanner is permitted to generate ultrasound image data for display on the multi-use electronic display device is further based on whether the approved scanner identifier matches the scanner identifier retrieved from the ultrasound scanner.

In some embodiments, the digital certificate encodes permission data associated with the approved scanner identifier, the permission data indicating an operation one or more of the ultrasound scanner and the multi-use electronic display device is capable of performing, and wherein the method further involves: based on the permission data, restricting the operation from being performed.

In another broad aspect of the present disclosure, there is provided a method of controlling operation of an ultrasound scanner with a multi-use electronic display device, the method involving the ultrasound scanner: sending a scanner identifier for the ultrasound scanner to the multi-use electronic display device, wherein the multi-use electronic display device sends the scanner identifier to a server; receiving a digital certificate from the multi-use electronic display device, the digital certificate having been received by the multi-use electronic display device in response to the sending of the scanner identifier to the server, and the digital certificate forwarded to the ultrasound scanner by the multi-use electronic display device; attempting to validate the received digital certificate; and controlling whether the ultrasound scanner is permitted to generate ultrasound image data for display on the multi-use electronic display device based on whether the ultrasound scanner successfully validates the received digital certificate.

In some embodiments, the ultrasound scanner is provided with a public key, and the attempting to validate the received digital certificate involves: determining whether the digital certificate was digitally signed with a private key corresponding to the public key.

In some embodiments, the digital certificate includes an approved scanner identifier, and the method further involves: determining whether the approved scanner identifier matches the scanner identifier sent to the multi-use electronic display device.

In some embodiments, upon a successful validation of the received digital certificate, the method further involves: encrypting communications between the ultrasound scanner and the multi-use electronic display device.

In another broad aspect of the present disclosure, there is provided a method of controlling operation of an ultrasound scanner with a multi-use electronic display device, the method involving, at a server: receiving a scanner identifier from the multi-use electronic display device, the scanner identifier having been retrieved by the multi-use electronic display device from an ultrasound scanner; determining an institution affiliation status of the ultrasound scanner; and sending the institution affiliation status of the ultrasound scanner to the multi-use electronic display device, wherein the multi-use electronic display device controls, based on the institution affiliation status, whether the ultrasound scanner is permitted to generate ultrasound image data for display on the multi-use electronic display device.

In some embodiments, the institution affiliation status indicates the ultrasound scanner is unaffiliated, and the method further involves: receiving a request from the multi-use electronic display device to link the ultrasound scanner to an institution account; updating the institution affiliation status of the ultrasound scanner to indicate the ultrasound scanner is affiliated with the institution account; and sending confirmation to the multi-use electronic display device that the institution affiliation status of the ultrasound scanner has been updated.

In some embodiments, the method further involves: sending a digital certificate to the multi-use electronic display device, wherein the controlling whether the ultrasound scanner is permitted to generate ultrasound image data for display on the multi-use electronic display device is further based on whether the digital certificate is successfully validated.

In some embodiments, the digital certificate is digitally signed with a private key, and a successful validation of the digital certificate requires possession of the public key corresponding to the private key.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a block diagram of a system for securing operation of an ultrasound scanner, in accordance with at least one embodiment of the present invention. The system 100 may include an ultrasound scanner 110 that is communicably connected (either through wired or wireless communication) to the multi-use electronic display device 120 (sometimes referred to just as "display device" herein). The display device 120 may also be communicably connected to a server 130 via network 106 (e.g., the Internet) to facilitate electronic communication.

The ultrasound scanner 110 may be configured to transmit ultrasound energy to a target object, receive ultrasound energy reflected from the target object, and generate ultrasound image data based on the reflected ultrasound energy. The ultrasound scanner 110 may include a transducer 115 which converts electric current into ultrasound energy and vice versa. Transducer 115 may transmit ultrasound energy to the target object which echoes off the tissue. The echoes may be detected by a sensor in transducer 115 and relayed through suitable electronics that interpret and process the echoes to generate image data of the scanned tissue. In some embodiments, the ultrasound scanner 110 may be provided as a handheld ultrasound probe that transmits the image data to the display device 120 for display thereon.

Ultrasound scanner 110 may include various components (not shown) for storing software or firmware instructions, configuration settings (e.g., sequence tables), and/or ultrasound image data. The ultrasound scanner 110 may also include one or more processors (not shown) for executing the instructions for performing acts of the methods discussed herein. In various embodiments, the acts performed by the ultrasound scanner 110 discussed herein may be provided in the form of a security module 112. The security module 112 may have access to a public key store 114. For example, as discussed below in relation to FIG. 3, a public key may be retrieved from the public key store 114 to validate a digital certificate when securing the operation of the ultrasound scanner 110.

Each ultrasound scanner 110 may also be provided with a unique scanner identifier 116. As discussed below, in some embodiments, an approved scanner identifier may be encoded into a digital certificate received by the ultrasound scanner 110, and controlling of operation of the ultrasound scanner 110 may include confirming that the approved scanner identifier encoded into a received digital certificate at the ultrasound scanner 110 matches the actual scanner identifier 116 of the ultrasound scanner 110.

Display device 120 may be a multi-use electronic display device such as a smartphone, tablet computer, or other suitable display device. In various embodiments, the display device 120 may be provided with an input component capable of receiving user input. Certain input received at the display device 120 may be relayed to ultrasound scanner 110 to control the operation of ultrasound scanner 110. Display device 120 may also include an output component, such as a display screen, which displays images based on image data acquired by ultrasound scanner 110. For example, the display device 120's input component may include a touch interface layered on top of the display screen of the output component. Electronic display device 120 may also include memory, Random Access Memory (RAM), Read Only Memory (ROM), and persistent storage device, which may all be connected to a bus to allow for communication therebetween and with one or more processors. Any number of these memory elements may store software and/or firmware that may be accessed and executed by the one or more processors to perform the methods and provide the user interfaces described herein as being performed by or provided on the display device 120.

In various embodiments, the display device 120 may execute an application that is configured to communicate with the ultrasound scanner 110. In FIG. 1, this is shown as scanner application or "scanner app" 122. This application 122 may also be generally referred to as the "ultrasound app" herein. For example, in embodiments where the multi-use electronic display device 120 provides a native software distribution platform (e.g., such as the Apple™ App Store™ for iOS™ devices or the Google™ Play Store™ for Android™ devices), the ultrasound app 122 may be downloaded therefrom. In an example embodiment, the scanner application 122 may be provided with a security and permissions module 124 configured to secure the operation of ultrasound scanners 110 attempting to connect to the display device 120. For example, the security and permissions module 124 may be configured to perform various acts of the methods described herein as being performed by the multi-use electronic display device 120.

The security and permissions module 124 may have access to a public key store 126 which stores public keys that may be used to validate digital certificates. As discussed below with respect to FIG. 3, in some embodiments, the scanner app 122 may be configured to validate a digital certificate as a part of its process for authenticating an ultrasound scanner 110 that is attempting to connect to it.

Server 130 may be configured to provide an activation and permissions service 132 to perform various acts of the methods discussed herein as being performed by the server 130. The server 130 may be configured to communicate with the display device 120 to provide institution affiliation status information, security information, and/or permissions information to the display device 120 with respect to the display device 120's interaction with a given ultrasound scanner 110. For example, these various items of information may be respectively stored in an institution affiliation status data store 134, a certificate store 136, and a permissions store 138. These example data stores are provided for illustration only; other configurations for storing this data may be possible.

During operation, the activation and permissions service 132 may access these various data stores 134, 136, 138 to retrieve the appropriate corresponding information that indicates to display device 120 whether and/or how it is to receive ultrasound image data from the ultrasound scanner 110. In various embodiments, the activation and permissions service 132 may be provided in the form of software instructions configured to execute on server 130. For example, the software instructions may provide an Application Programming Interface (API) that the security and permissions module 124 on the scanner app 122 is configured to access prior to allowing the receipt of ultrasound image data from a given ultrasound scanner 110.

Figure 2:
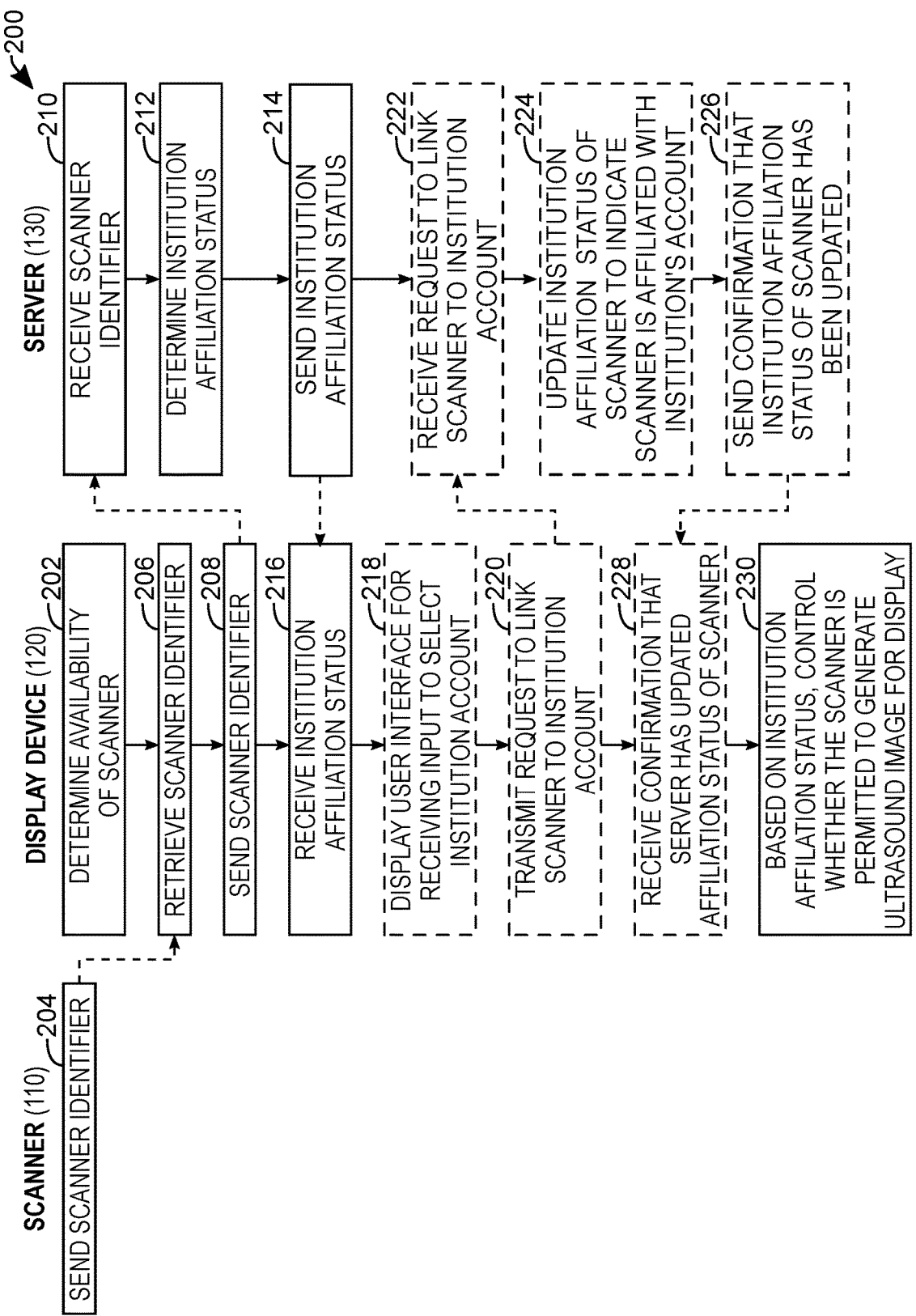
FIG. 2 is a flowchart diagram showing acts for securing operation of an ultrasound scanner based on an institution affiliation status, in accordance with at least one embodiment of the present invention.

Referring to FIG. 2, shown there generally as 200 is a flowchart diagram showing acts for securing operation of an ultrasound scanner based on an institution affiliation status, in accordance with at least one embodiment of the present invention. In discussing the embodiments of FIG. 2, reference will also be made to the components in the system of FIG. 1. For example, as illustrated, FIG. 2 shows the acts being performed by the ultrasound scanner 110, display device 120, and server 130 illustrated in the system of FIG. 1. FIG. 2 also shows interactions amongst these various components of the system 100.

In various embodiments, the acts shown as being performed by the ultrasound scanner 110 in FIG. 2 may be performed by the security module 112 executing on ultrasound scanner 110. Similarly, the acts shown as being performed by the display device 120 may be performed by the security and permissions module 124 of the scanner app 122 executing on the display device 120. Further, the acts shown as being performed by the server 130 may be performed by the activation and permissions service 132 executing on the server 130.

At 202, a multi-use electronic display device 120 may determine the availability of an ultrasound scanner 110 for connecting to the display device 120. This may be performed in various ways. For example, if the ultrasound scanner 110 is a wired ultrasound probe to be connected to a port provided on the display device 120, the display device 120 may determine that the ultrasound probe is available upon the physical connection of the ultrasound probe to the display device 120. In another example, if the ultrasound scanner 110 is to be connected to the display device 120 wirelessly, the display device 120 may determine the availability of the ultrasound scanner 110 if the ultrasound scanner 110 is powered on and within the proximity of the display device 120. For example, the ultrasound scanner 110 may be configured to advertise its availability for connection via wireless communication protocols such as Bluetooth™ or Wi-Fi™.

At 204, the ultrasound scanner 110 may send its scanner identifier to the display device 120. The display device 120 may retrieve and receive the scanner identifier (act 206). For example, the sending of the scanner identifier by the scanner 110 may be performed as a part of an existing pairing, discovery, and/or handshake process between the scanner 110 and the display device 120.

At 208, the display device 120 may send/forward the scanner identifier to the server 130 for determining an institution affiliation status of the ultrasound scanner associated with the scanner identifier. The server 130 may then receive the scanner identifier (act 210).

At 212, the server 130 may determine an institution affiliation status of the ultrasound scanner 110. The server 130 may then send the institution affiliation status of the ultrasound scanner 110 to the multi-use electronic display device 120 (act 214). At 216, the display device 120 may receive the institution affiliation status of the ultrasound scanner 110.

As used herein, the term "institution" may refer to a hospital, clinic, medical practice, or any other collection of users who may use an ultrasound scanner 110. In some embodiments, an "institution" may also have a single user. In some embodiments, institutions may be provided in a tiered or nested fashion. For example, an institution may have internal departments, divisions, or the like; and an ultrasound scanner 110 may additionally or alternatively be associated with one or more such departments or divisions within an institution. In various embodiments, the acts discussed below for determining and controlling use of a scanner 110 based on the institution affiliation status may involve determining and controlling use based on department or division affiliation status.

In various embodiments, the multi-use display device 120 may be associated with an institution account. In various embodiments, this association may be fixed or dynamic. For example, a fixed association may occur if an institution purchases a fleet of display devices 120 for use with ultrasound scanners 110, and registers a device identifier (e.g., Media Access Control (MAC) address) of the display devices 120 as being associated with a given institution account at the server 130. Once registered, the server 130 may return an institution account identifier to the display device 120 (e.g., as may be received by the scanner app 122) so that the display device 120 is aware of the institution account identifier it is associated with.

Additionally or alternatively, the association between the display device 120 and the institution account may be dynamic. For example, a dynamic association may occur if the association is provided by a user account logged into the scanner app 122 executing on the display device 120. In this example, the association between the display device 120 and the institution account can be changed based on the user account that is logged into the scanner app 122. The user account may be linked to the institution account. By virtue of a given user account being logged into the scanner app 122, the display device 120 may be considered as being associated with the institution account of the user account. In this example, the scanner app 122 may thus also have access to an institution account identifier of the logged-in user account.

Referring still to FIG. 2, the institution affiliation status of a scanner 110 received at act 216 may be used to control the operation of the scanner 110. For example, in some embodiments, the institution affiliation status of a given scanner 110 may indicate the scanner 110 is already affiliated with an institution account. The display device 120 may then skip over acts 218-228 and proceed to act 230.

At act 230, the display device 120 may control, based on the institution affiliation status received at act 216, whether the scanner 110 is permitted to generate ultrasound images for display. For example, if the institution affiliation status indicates the ultrasound scanner 110 is affiliated with the institution account of the display device 120 (e.g., the ultrasound scanner's 110 institution affiliation matches the institution account of the display device 120), the ultrasound scanner may be permitted to generate ultrasound image data for display on the multi-use electronic display device 120. For example, by confirming that the institution affiliation status of an ultrasound scanner 110 matches the institution account associated with the display device 120 prior to permitting operation of the scanner 110 with the display device 120, the likelihood of unauthorized operation of the ultrasound scanner 110 may be reduced.

However, if the institution affiliation status indicates the ultrasound scanner 110 is affiliated with another institution account different from the institution account associated with the multi-use electronic display device 120, the ultrasound scanner 110 can be prevented from generating ultrasound image data for display on the multi-use electronic display device 120.

Figure 6:
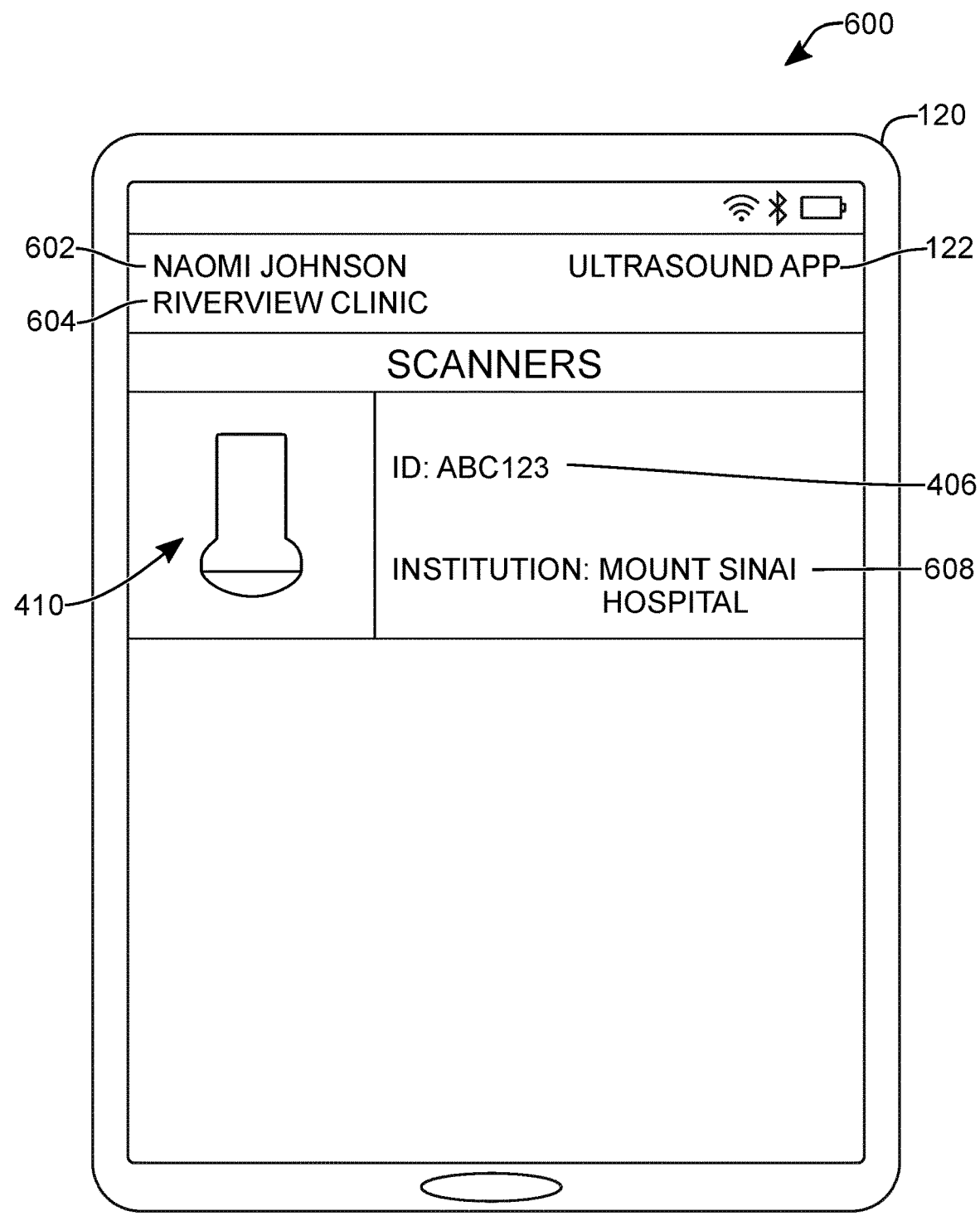
FIGS. 6-7 are example screenshots of a user interface on a multi-use electronic display device when it connects to an ultrasound scanner affiliated with an institution account different from the institution account associated with the multi-use electronic display device, in accordance with at least one embodiment of the present invention.

Referring simultaneously to FIG. 6, shown there generally as 600 is an example screenshot of a user interface on a multi-use electronic display device 120 when it connects to an ultrasound scanner affiliated with an institution account different from the institution account associated with the multi-use electronic display device 120, in accordance with at least one embodiment of the present invention. As shown in FIG. 6, an ultrasound app 122 may be executing on the display device 120. In this embodiment, the institution account associated with the display device 120 may be provided by way of a logged-in user. As illustrated, the logged-in user "Naomi Johnson" 602 and an institution account "Riverview Clinic" 604 they belong to may be shown in the upper left-hand corner of the user interface of the ultrasound app 122. The ultrasound app 122 may display the available scanners for pairing and connecting. As shown, a scanner 410 with scanner identifier "ABC123" 406 is shown. The institution affiliation status retrieved from the server 130 in this instance may indicate that the scanner 410 is affiliated with the institution "Mount Sinai Hospital" 608.

Figure 7:
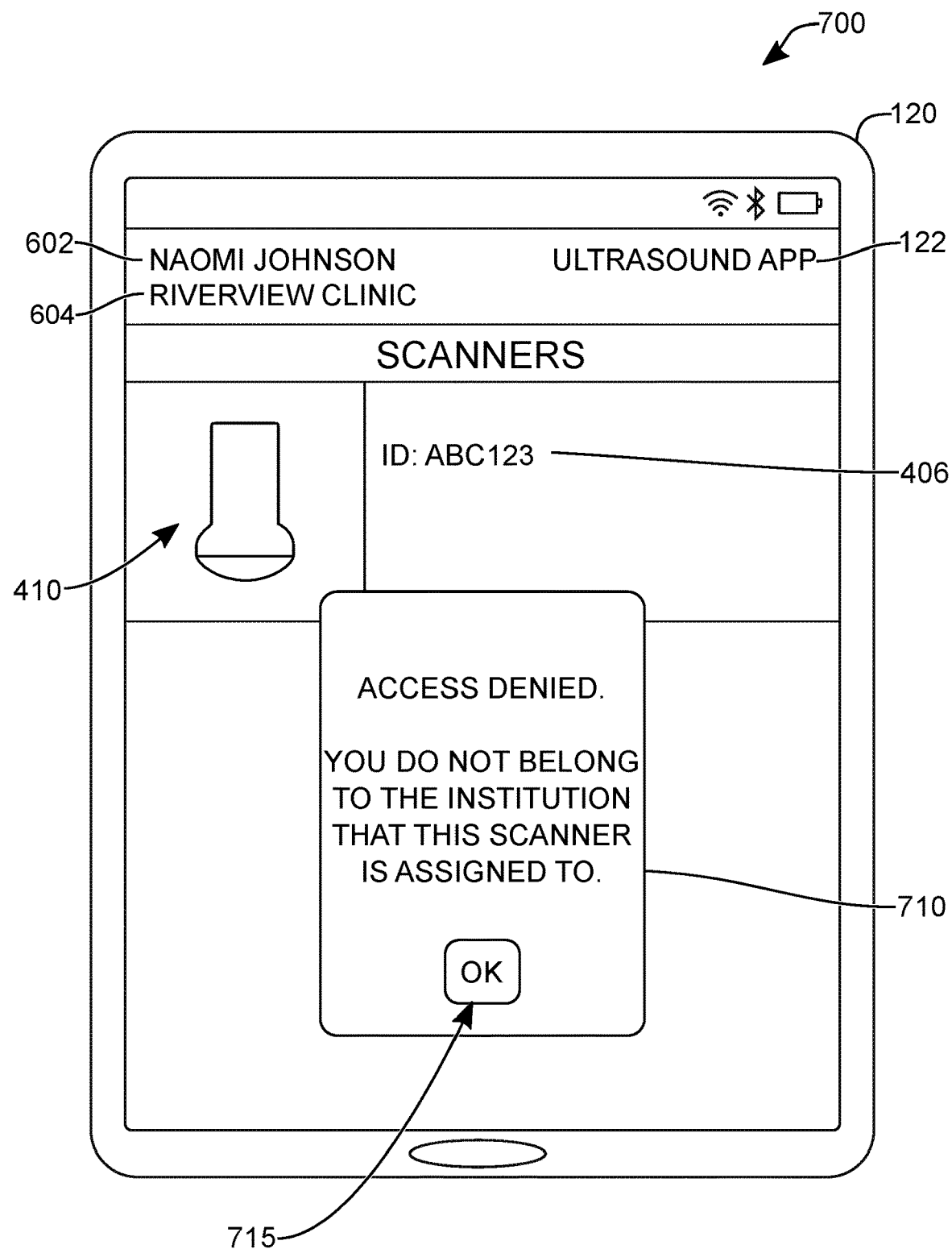

Referring to FIG. 7, shown there generally as 700 is another example screenshot of a user interface on a multi-use electronic display device 120 when it connects to an ultrasound scanner affiliated with an institution account different from the institution account associated with the multi-use electronic display device 120, in accordance with at least one embodiment of the present invention. For example, the user interface of FIG. 7 may be shown if input is received in the user interface of FIG. 6 to select use of the ultrasound scanner 410 with scanner identifier "ABC123" 406. Since the scanner 410 is affiliated with an institution account (e.g., "Mount Sinai Hospital" 608) that is different from the institution account of the display device 120 ("Riverview Clinic" 604), the display device 120 may prevent the ultrasound scanner 410 from generating ultrasound image data for display on the display device 120. In the embodiment shown in FIG. 7, the denial may be provided by the display device 120 in the form of a message dialog 710 (with the message "Access Denied. You do not belong to the institution that this scanner is assigned to.") shown by the ultrasound app 122.

Even though the user interface of FIG. 7 may generally be shown at a point in time after the selection of scanner 410 shown in FIG. 6, some changes have been made to the example screenshot of FIG. 7 to illustrate different possible implementations. As shown in FIG. 6, the institution account that the scanner 410 is affiliated with is shown as "Mount Sinai Hospital" 608. However, this may potentially be omitted when the ultrasound app 122 shows ultrasound scanners 410 available for connection. For example, as shown in FIG. 7, the institution account affiliated with the scanner 410 is not shown. Nevertheless, the message 710 indicating that access is denied can be shown because the institution account 604 of the display device 120 is different from that affiliated with the scanner 410. Omitting the display of the institution account that the scanner 110 is affiliated with may, for example, make it more difficult for an unauthorized user to spoof a linkage between the institution account and the display device 120 when there in fact is not such a linkage.

Referring still to FIG. 7, the example message dialog 710 has an 'OK' button 715 to dismiss the message dialog. However, in some embodiments, the message dialog may be configured to include a 'Request to Join' button that allows a user to request to join the institution account that the ultrasound scanner 410 is affiliated with. A 'Request to Join' option may facilitate ease of adding new staff to a particular institution. For example, when new medical staff joins an institution, they may attempt to use the scanners 110 that are available for connection at the site of the institution. However, if they have not been pre-added to the institution account of the institution, they may be denied access to use of the scanners 110. The 'Request to Join' option may thus allow the user to initiate the process of being added to the institution account within the ultrasound app 122 without requiring the user to contact a scanner 110 administrator through some outside means such as email or telephone. At the same time, the 'Request to Join' option may still preserve the ability to secure operation of ultrasound scanners 110 based on the institution affiliation status of the scanner 110.

In the example screenshots shown in FIGS. 6 and 7, a given user account is shown as being affiliated with a single institution account. However, in various embodiments, a user account may be linked to multiple institution accounts. For example, this may be possible if a user works at multiple workplaces (e.g., a clinic and a hospital). In some such embodiments, the scanners 110 associated with any of the user account's institution accounts may be used by the user. Alternatively, as discussed below with respect to FIG. 9, an administrator for an institution may assign users to certain scanners 110. In such case, a given user may also need to be an assigned user for a given scanner 110 (in addition to being associated with the same institution) to be able to use it.

The screenshots of FIGS. 6 and 7 show one example embodiment of how access to the scanner 410 can be denied. However, other methods of denying access may be possible. For example, as shown in FIG. 6, the scanner 410 is shown in the list of available scanners for connection even though the scanner 410 is affiliated with an institution account that is different from that of the display device 120 (e.g., dynamically by virtue of the logged-in user). In some embodiments, if the ultrasound app 122 determines a scanner 110 is affiliated with an institution account that is different from any institution account that the display device 120 is linked to, the ultrasound app 122 may omit the scanner 110 from the list of available scanners 110 available for connection altogether. This embodiment may enhance security of the scanner 110 and reduce the likelihood of an unauthorized user attempting to user the scanner 110 since they would not be able to see it in their list of scanners for connection.

Referring back to FIG. 2, steps 218-228 will now be discussed. As noted above, the institution affiliation status of an ultrasound scanner 110 may indicate the institution account that the scanner 110 is associated with. However, in some embodiments, the institution affiliation status received at 216 may instead indicate that the scanner 110 is unaffiliated with any institution account at all. A given ultrasound scanner 110 may be in an unaffiliated state, for example, when the scanner is first shipped from the manufacturer of the ultrasound scanner 110. In another example, as discussed below in relation to FIG. 9, the server 130 may provide a scanner administration portal that allows a scanner 110 to be released from an affiliated institution account. Once released, the scanner 110 may return to an unaffiliated status. Acts 218-228 are shown in dotted outline because they are optional, and may only be performed by a display device 120 if the institution affiliation status received at act 216 indicates the scanner is unaffiliated.

Figure 4:
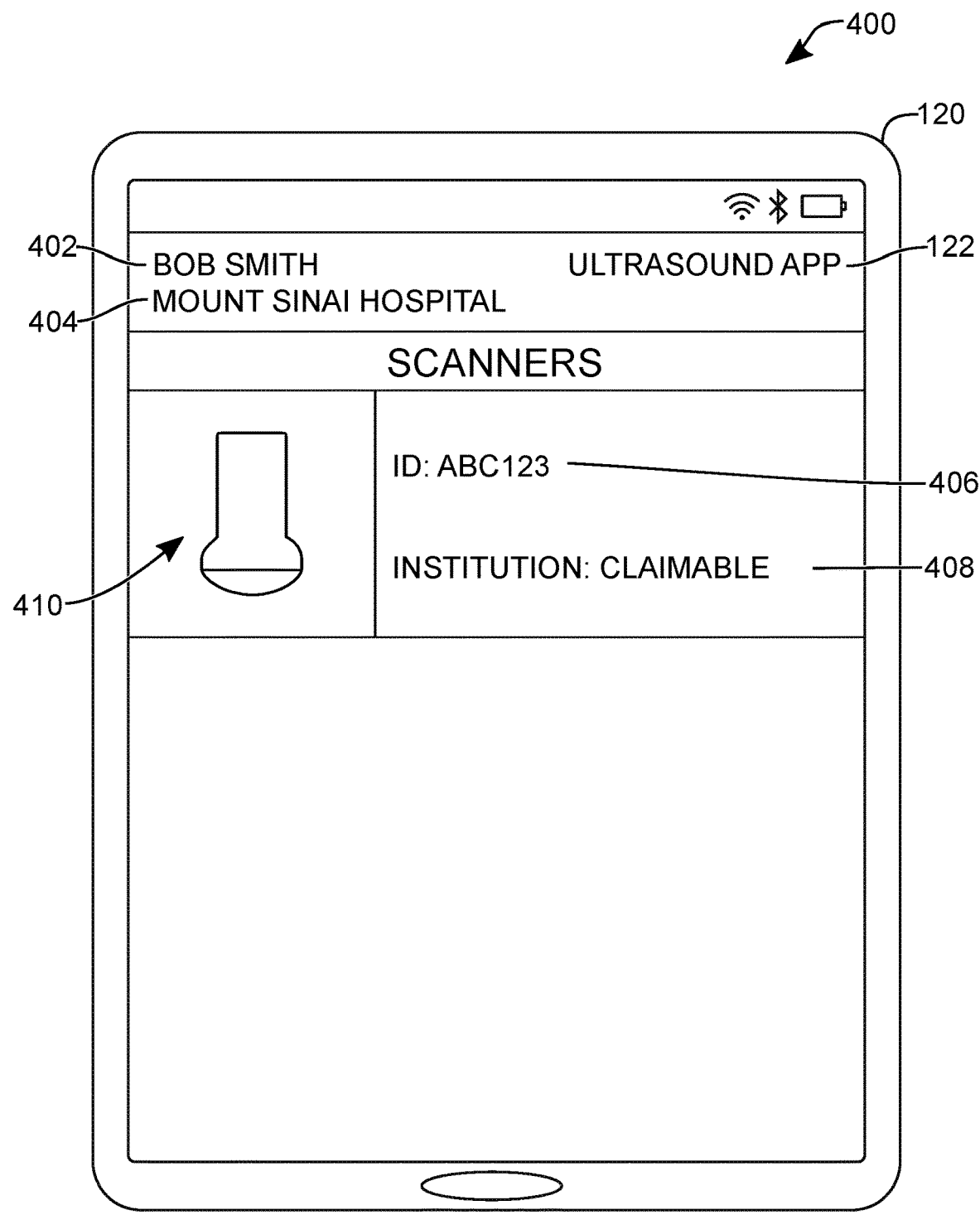
FIG. 4 is an example screenshot of a user interface on a multi-use electronic display device when it connects to an ultrasound scanner that is unaffiliated, in accordance with at least one embodiment of the present invention.

At 218, the display device 120 may display a user interface for receiving input to select the institution account to be affiliated with the scanner 110 having the scanner identifier retrieved at act 206. Referring simultaneously to FIG. 4, shown there generally as 400 is an example screenshot of a user interface on a multi-use electronic display device when it connects to an ultrasound scanner that is unaffiliated, in accordance with at least one embodiment of the present invention. Similar to the example screenshot discussed above in relation to FIG. 6, the user interface in FIG. 4 shows an ultrasound app 122 executing on display device 120. The display device 120 may be dynamically associated with an institution account (e.g., "Mount Sinai Hospital" 404) by way of a logged-in user (e.g., "Bob Smith" 402).

In the embodiment of FIG. 4, the ultrasound app 122 may be configured to show a list of scanners 410 available for connection. In FIG. 4, a scanner 410 is shown as being available for connection. However, unlike the example screenshot of FIG. 6, the scanner 410 is unaffiliated and not already affiliated with an institution account. As shown, the scanner identifier is "ABC123" 406. However, no institution account is shown; instead, the scanner is shown as "Claimable" 408 to indicate that the scanner is unclaimed and may be linked to an institution account.

Figure 5:
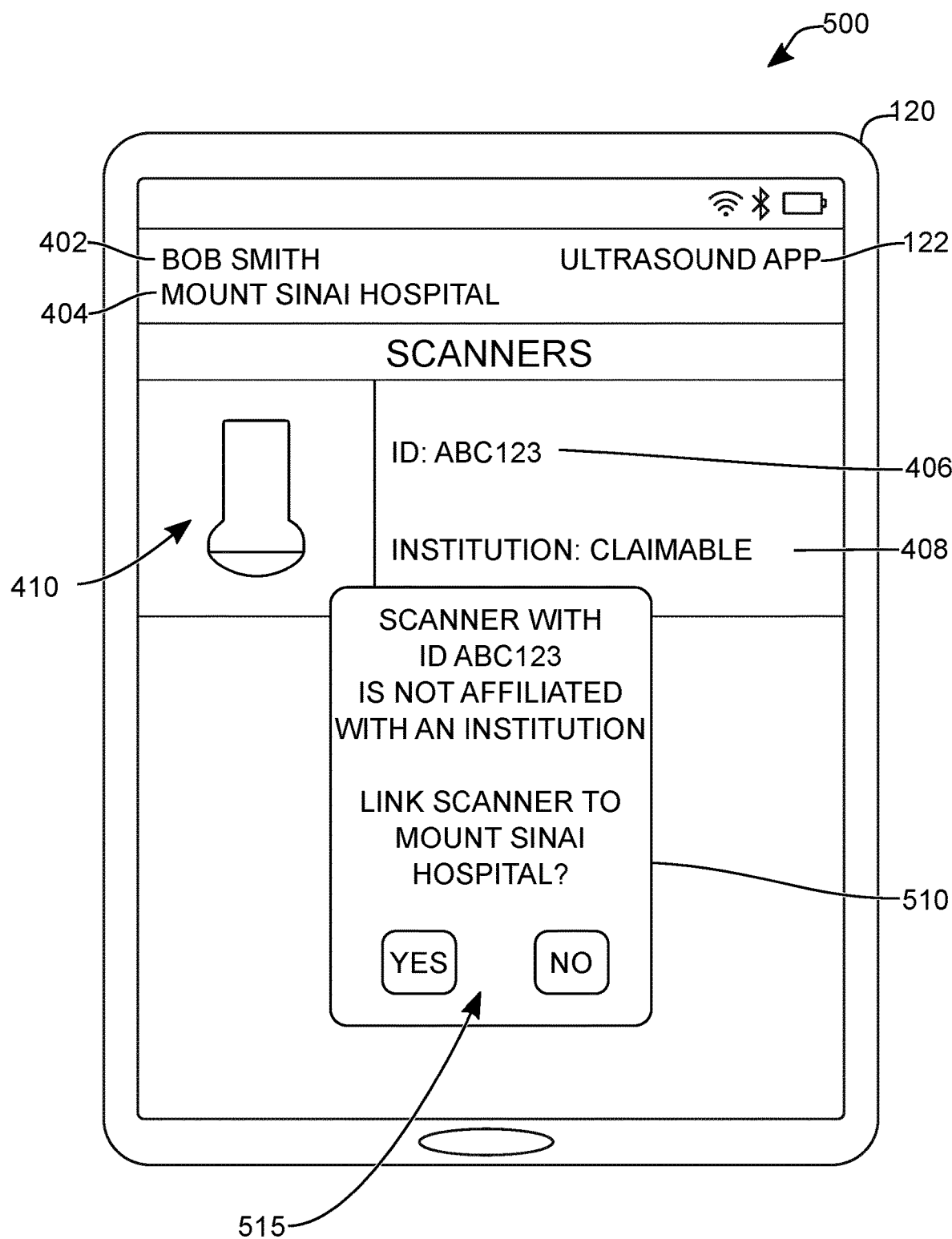
FIG. 5 is an example screenshot of a user interface on a multi-use electronic display device when it requests to link an unaffiliated ultrasound scanner to an institution account, in accordance with at least one embodiment of the present invention.

Referring to FIG. 5, shown there generally as 500 is an example screenshot of a user interface on a multi-use electronic display device when it requests to link an unaffiliated ultrasound scanner to an institution account, in accordance with at least one embodiment of the present invention. The example user interface of FIG. 5 may be shown if the scanner 410 in the user interface of FIG. 4 is selected. Once selected, the ultrasound app 122 may prompt the user to input an institution account to which they would like to link the scanner 410. For example, since in FIG. 4, the display device 120 is already linked to the institution account "Mount Sinai Hospital 404", the example screenshot of FIG. 5 may display a message 510 indicating "Scanner with ID ABC123 is not affiliated with an institution. Link scanner to Mount Sinai Hospital?", with options 515 to respond "Yes" or "No".

The example user interfaces shown in FIGS. 4 and 5 are only examples of how an ultrasound app 122 may provide an indication that a scanner available for connection is unaffiliated with an institution account. Various other user interfaces may be provided to perform similar tasks. For example, as noted above, it may be possible that a display device 120 is associated with multiple institution accounts (e.g., if the association of a display device 120 with institution accounts is provided by way of a logged-in user, and the logged-in user is associated with multiple institution accounts). In this case, instead of the message shown in FIG. 5, the ultrasound app 122 may display a list of institution accounts the display device 120 is associated with, for selection of the institution account that the ultrasound scanner 410 is to be linked to.

Referring back to FIG. 2, at 220, once display device 120 has received input indicating the institution account, it may transmit a request to the server 130 to link the ultrasound scanner 110 to the institution account associated with the multi-use electronic display device 120. This request to link the ultrasound scanner 110 to the institution account may then be received at the server 130 (act 222).

At 224, the server 130 may update the institution affiliation status of the ultrasound scanner 110 to indicate the ultrasound scanner is affiliated with the institution account. For example, this act may involve changing the entry in the institution affiliation status store 134 (as shown in FIG. 1) for the scanner 110 from an unaffiliated status to a linked status indicating the scanner is now linked to the desired institution account.

At 226, the server 130 may send confirmation to the multi-use electronic display device 120 that the institution affiliation status of the ultrasound scanner 110 has been updated. This confirmation may be received at the display device 120 (act 228). The method may then proceed to act 230 and, based on the institution affiliation status, control whether the ultrasound scanner 110 is permitted to generate ultrasound image data for display on the multi-use electronic display device 120. Since the display device 120 has been able to confirm that the scanner 110 has now been linked to an institution account that matches that which is associated with the display device 120, act 230 may include permitting the ultrasound scanner to generate ultrasound image data for display on the multi-use electronic display device 120.

In the example embodiments of FIGS. 4 and 5 described above, the display device 120 was already affiliated with an institution account (e.g., dynamically by way of a logged-in user). However, in some embodiments, it is possible that when a scanner 110 is first determined to be available for connection by a display device 120, the display device 120 is not yet associated with an institution account. In such case, the display device 120 may be configured to receive input to select the institution account to be associated with the display device 120. Additionally or alternatively, the display device 120 may be configured to receive input to create a new institution account.

Figure 8:
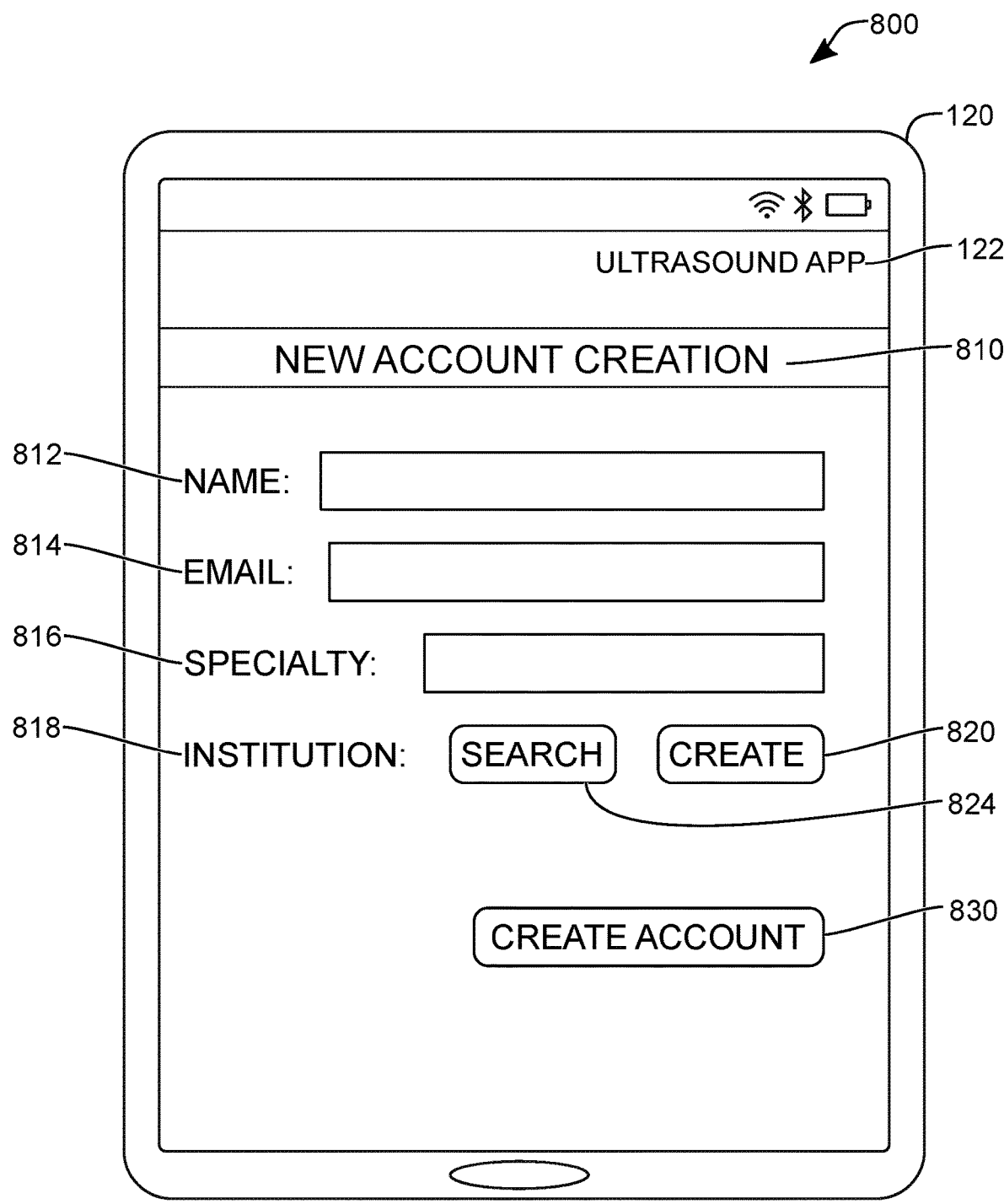
FIG. 8 is an example screenshot of a user interface on a multi-use electronic display for creating a user account, in accordance with at least one embodiment of the present invention.

Referring to FIG. 8, shown there generally as 800 is an example screenshot of a user interface on a multi-use electronic display for creating a user account, in accordance with at least one embodiment of the present invention. FIG. 8 illustrates the execution of the example ultrasound app 122 shown previously in FIGS. 4-7. However, unlike those other user interfaces, no user account nor institution account is shown in the upper left-hand corner. The ultrasound app 122 may thus provide functionality for creating a new account through the "New Account Creation" user interface 810 shown in FIG. 8. As shown, the user interface may contain text fields for inputting name 812, email 814, and medical specialty 816. For the institution 818 the user account is to be linked to, the user interface may provide an ability to "Search" 824 for an existing institution account to join or "Create" 820 a new institution account. Upon successful completion of the necessary fields and inputting of data, the "Create Account" button 830 may be activated to create the account.

As noted above, the display device 120 can be associated with an institution account directly (e.g., in a fixed manner, through registration of a display device identifier with an institution account at the server 130) or indirectly (e.g., dynamically, via a logged-in user account's linked institution account(s)). The example screenshot of FIG. 8 shows an example of the latter scenario. However, in various embodiments, the latter scenario may be implemented in different ways.

For example, as shown in FIG. 8, the new account creation user interface may provide an option of searching for 824 or creating 820 a new institution account. However, in various embodiments, the functions of creating a new user account and associating the user account with an institution may be separated. In such case, the new account creation user interface may omit user interface fields 818 for searching for 824 or creating 820 an institution account. The user interface may instead provide an alternative user interface for associating with an institution account. Additionally or alternatively, the ability to "Search" 824 for an institution account to join may not be provided at all. For example, this may be the case if membership in an institution account is available on an "invitation only" basis, such that the administrator of an institution account is provided with an option (e.g., through a web interface on server 130) to invite new users to join in an institution account.

In yet another embodiment, the user interface option to "Create" 820 an institution account may not necessarily be provided in the context of a user account's settings. Instead, referring back simultaneously to FIG. 5, when the ultrasound app 122 is supplied input selecting to connect to an ultrasound scanner 410 that is unaffiliated, the ultrasound app 122 may, at that point, present a user interface option to create a new institution account to link the unaffiliated ultrasound scanner 410 to. As shown in FIG. 5, this may mean the message 510 is provided with a third response option: e.g., in addition to 'Yes' and 'No' options 515 for linking to an existing institution account of the user account, there may be a third option for creating a new institution account provided on that message 510. Various other options for providing a user interface to associate a display device 120 and/or user account to an institution account (or for creating an institution account) may be possible.

Figure 9:
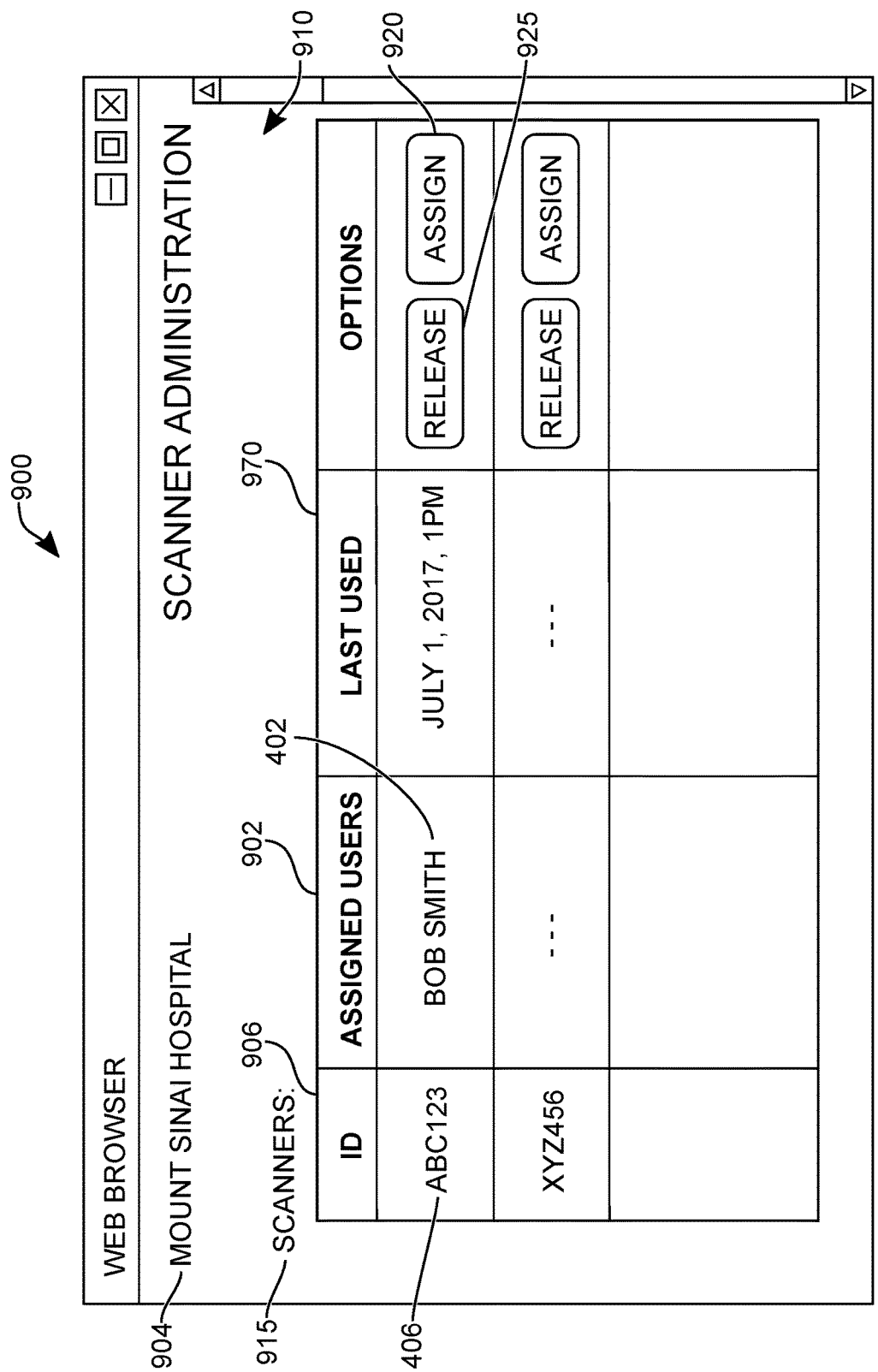
FIG. 9 is an example screenshot of a user interface for administration of ultrasound scanners, in accordance with at least one embodiment of the present invention.

Referring to FIG. 9, shown there generally as 900 is an example screenshot of a user interface for administration of ultrasound scanners, in accordance with at least one embodiment of the present invention. As noted above, the server 130 (as shown in FIG. 1) may provide a scanner administration user interface to provide administration functions for the scanners 110 that are affiliated with a given institution account. For example, the user interface of FIG. 9 may be provided by the activation and permissions service 132 of the server 130.

In the user interface of FIG. 9, an example "Scanner Administration" webpage 910 is shown. The institution account for the scanner administration webpage 910 may be provided in the upper-left hand corner of the webpage (e.g., "Mount Sinai Hospital" 904). A list of affiliated scanners 915 may be listed in the form of a table with columns for scanner identifier 906, assigned users 902, a last-used timestamp for the scanner 970, and administrator options for a given scanner 110.

The example user interface of FIG. 9 continues with the example scenarios discussed earlier with respect to FIGS. 6 and 7 where a scanner 410 with scanner identifier "ABC123" 406 is affiliated with the "Mount Sinai Hospital" 904 institution. Because of this affiliation, this scanner 410 will be listed in the scanner list 915 for the scanner administration webpage of the "Mount Sinai Hospital" 904 institution. In the example user interface, another scanner with scanner identifier "XYZ456" may also be affiliated with the "Mount Sinai Hospital" 904 institution, and thus be also listed. The entry for a given scanner 110 may provide various administration information or functions related to the scanner.

For example, there may be information about the last time the scanner was used (e.g., "Jul. 1, 2017 1 PM" for the scanner 410 with scanner identifier 406).

There may also be an option to "Release" 925 a scanner 110 from the institution account. As noted above, an administrator may wish to release a scanner 110 from an institution account if, for example, the owner of the scanner owner desires to allow another institution to claim the scanner and be affiliated with it. For example, this may happen if a scanner is sold or gifted to another institution.

Another administration function that is illustrated in FIG. 9 is the ability to "Assign" users 920 to a given scanner identifier. In various embodiments, the assigned users function is optional, and when provided, may allow an administrator to limit which users (that are already linked to an institution account) are to have access to a given scanner 110 with a given scanner identifier. For example, as shown in FIG. 9, the scanner 410 with scanner identifier "ABC123" 406 has user account "Bob Smith" 402 as an assigned user. The administrator may then use the "Assign" button 920 to assign additional users that are linked to the institution account to the scanner 410 with scanner identifier "ABC123" 406.

If the institution account has enabled the feature to limit access of certain scanners 110 to only assigned users, then users who are not within the assigned users list 902 for a given scanner 110 may be prevented from using the scanner 110 and generating imaging data when they are logged into a display device 120. This is so even though the institution account their user account is associated with matches the institution account of the scanner 110. By providing this additional layer of user-based security, the present embodiments may provide enhanced security that requires: the display device 120 to be associated with the same institution account that the scanner is affiliated with (e.g., dynamically, by way of a logged-in user), and also, that the logged-in user be assigned to use the scanner by an administrator of the institution account.

If this optional feature is not turned on, any user account that is linked to an institution account matching the institution account of a scanner 110 may be permitted to use the scanner 110 for generating and display ultrasound images (when that user account is logged into a display device 120).

Figure 3:
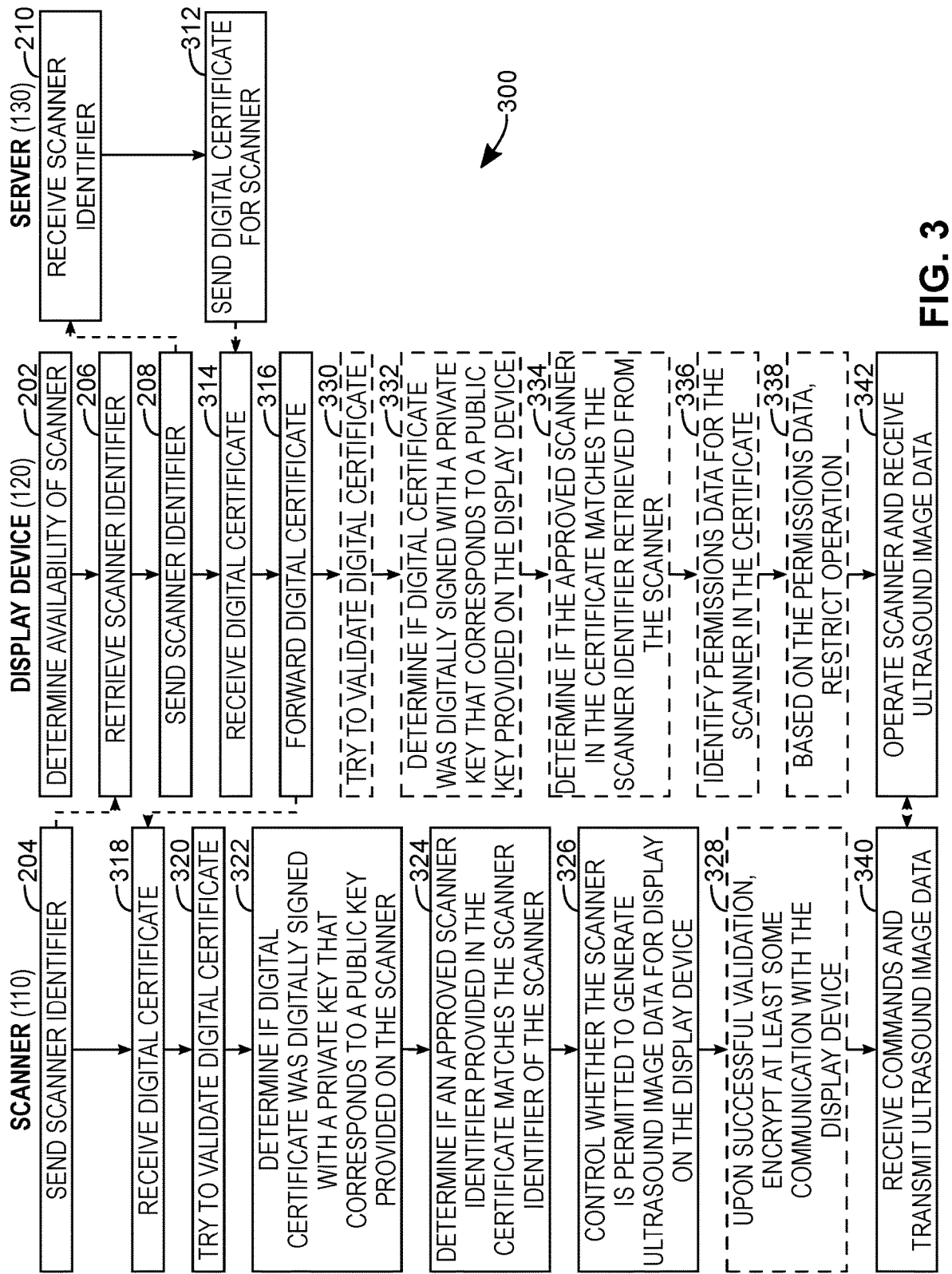
FIG. 3 is a flowchart diagram showing acts for securing operation of an ultrasound scanner based on validation of a digital certificate, in accordance with at least one embodiment of the present invention.

Referring to FIG. 3, shown there generally as 300 is a flowchart diagram for acts of a method for securing operation of an ultrasound scanner based on validation of a digital certificate, in accordance with at least one embodiment of the present invention. FIG. 3 illustrates another method of securing operation of an ultrasound scanner. As discussed below, various acts of the method of FIG. 3 may be performed in addition to or instead of certain acts of the method of FIG. 2.

Similar to FIG. 2, FIG. 3 shows various acts being performed by the ultrasound scanner 110, display device 120, and server 130 shown in the system of FIG. 1. FIG. 3 also similarly shows interactions amongst the various components of the system 100. In discussing the embodiments of FIG. 3, reference will also be made to the components in the system of FIG. 1. For example, in various embodiments, the acts shown as being performed by the ultrasound scanner 110 in FIG. 3 may be performed by the security module 112 executing on the scanner 110. Similarly, the acts shown as being performed by the display device 120 may be performed by the security and permissions module 124 of the scanner app 122 executing on the display device 120. Further, the acts shown as being performed by the server 130 may be performed by the activation and permissions service 132 executing on the server 130.

In FIG. 3, acts 202-210 may be performed in a manner similar to that described above for FIG. 2. These acts relate generally to the display device 120 determining availability of a scanner 110 for connection, retrieving a scanner identifier 116 from the scanner 110, and sending/forwarding the scanner identifier to the server 130.

Once the server 130 is in possession of the scanner identifier, it may send a digital certificate for the scanner 110 having that scanner identifier to the display device 120 (act 312). For example, the certificate may be retrieved from the certificate store 136 (as shown in FIG. 1).

The digital certificate may be received at the display device 120 (act 314). The digital certificate may then be forwarded to the scanner 110 at act 316, and received at the scanner 110 (act 318). As discussed below, the controlling of whether the ultrasound scanner 110 is permitted to generate ultrasound image data for display on the multi-use electronic display device 120 can be based on whether the digital certificate is successfully validated. Also as discussed below, attempts to validate the digital certificate can be made at either or both of the scanner 110 and the display device 120, and the controlling of whether the scanner can be used to generate ultrasound images for display on the display device 120 can be based on whether the digital certificate is successfully validated at either one or both of the scanner 110 and the display device 120.

Acts 320-326 relate generally to validation of the digital certificate at the scanner 110. Acts 330-338 relate generally to validation of the digital certificate at the display device 120. While both sets of acts are shown in FIG. 3 and discussed below for illustration purposes, either set of acts may be omitted in various embodiments. For example, as shown in FIG. 3, acts 330-338 are shown in dotted outline to indicate that they may not be performed.

At 320, the scanner 110 may attempt to validate the received digital certificate. In cryptography, a digital certificate (also referred to as a public key certificate or identity certificate) can be considered an electronic document that can be used to prove the ownership of a public key. A digital certificate may include various information about the public key, the identity of the owner of the public key, and a digital signature of the entity that has verified the certificate's contents.

As will be understood by persons skilled in the art, validating the digital certificate may include validating the certificate's digital signature. Successful validation of the digital signature may allow the entity performing the validation to confirm at least: that the certificate was indeed sent by the expected sender (e.g., that the certificate is authentic and not spoofed); and that the message was not altered in transit (e.g., that the contents of the certificate are as they were when the certificate was sent by the sender).

To digitally sign the certificate, the server 130 may take a hash (e.g., using hash functions such as Message Digest 2, 4, or 5 (MD2, MD4, MD5) or Secure Hash Algorithm (SHA)) of the certificate, and encrypt the hash using a private key. In various embodiments, this private key may be the private key of the scanner 110's manufacturer. When the digitally signed certificate is then transmitted, the digital certificate may contain both the original contents of the digital certificate, along with the encrypted hash.

When the digital certificate is then attempted to be validated after transmission, the verifier may take a hash of the digital certificate using the same hash algorithm used by the sender. Separately, they may attempt to decrypt the hash portion of the digital certificate using the public key of the expected sender. If the decrypted hash matches the hash generated by the verifier, then the digital signature is considered to be successfully validated. If the hashes do not match, then the certificate has either been tampered with or the signature was digitally signed with a private key that does not correspond to the public key of the expected sender (and therefore, the digital certificate is not authentic).

Referring still to FIG. 3, at 322, the scanner 110 may determine whether the digital certificate was digitally signed with a private key corresponding to the public key. Referring simultaneously to FIG. 1, the scanner 110 may be provided with a public key store 114 that stores public keys accessible by security module 112. For example, the public key store 114 may be pre-loaded with the manufacturer's public key during manufacturing of the scanner 110. When validating the digital certificate, the scanner 110 may then use this public key to determine if the digital certificate received at act 318 was digitally signed with the manufacturer's corresponding private key. If the certificate's digital signature successfully validates, the method may proceed to act 324.

In some embodiments, the digital certificate may include information about an approved scanner identifier. If so, act 324 may be performed to determine if the approved scanner identifier provided in the certificate matches the scanner identifier of the scanner 110.

At 326, the scanner may control whether it is permitted to generate ultrasound image data for display on the multi-use electronic display device 120. In some embodiments, this may be based on whether the ultrasound scanner 110 successfully validates the received digital certificate (acts 320-322) and/or, if the certificate contains an approved scanner identifier, whether the approved scanner identifier matches the scanner 110's scanner identifier.

In various embodiments, control of whether the scanner is allowed to be used may be performed based on a successful validation of the certificate alone without inclusion of an approved scanner identifier in the certificate. For example, simply validating a digital certificate may help ensure that the scanner is not used with unauthorized software executing on the display device 110. For example, unauthorized software may include pirated software or software that has not been properly tested for safety standards.

However, including the approved scanner identifier in the certificate and confirming that it matches to the scanner's scanner identifier may provide an additional layer of security that ensures that the server 130 has authorized a particular scanner 110 to be used with the display device 120. For example, in embodiments where the scanner app 122 executing on display device 120 requires a user to log in to a user account, and the user account is only permitted to use a limited set of scanners 110, the inclusion of a scanner identifier in the digital certificate may provide a way for the server 130 to indicate and control which scanners 110 the user account is authorized is use. This may happen, for example, if scanners 110 are approved for use on a per-user-account basis: e.g., directly via the user account, or as discussed above, via association with an institution account or as an assigned user with an institution account.

At 328, upon a successful validation of the received digital certificate and/or matching of an approved scanner identifier to a scanner's scanner identifier, it may be possible to encrypt communications between the ultrasound scanner 110 and the multi-use electronic display device 120. For example, a symmetric encryption key may be exchanged and used for encrypting subsequent communications therebetween. This optional step is shown in dotted outline.

As noted above, it may be possible in some embodiments to secure operation of the scanner 110 based on validation of the digital certificate at the scanner 110. However, in some embodiments, acts to validate the digital certificate at the display device 120 may also be performed. These optional acts 330-338 are discussed below.

At 330, the display device 120 may attempt to validate the digital certificate. As with the validation at the scanner 110, this may involve determining whether the digital certificate was digitally signed with a private key corresponding to the public key of an expected sender (act 332).

Referring simultaneously to FIG. 1, the scanner app 122 may be provided with a public key store 126 that stores public keys accessible by the security and permissions module 124. For example, the public key store 126 may be pre-loaded with the manufacturer's public key before the scanner app 122 is made downloadable to the display device 120. When validating the digital certificate, scanner app 122 may then use this public key to determine if the digital certificate was digitally signed with the manufacturer's corresponding private key. If the certificate's digital signature successfully validates, the method may proceed to act 334.

As noted above, in some embodiments, the digital certificate may include information about an approved scanner identifier. If so, act 334 may optionally be performed to determine if the approved scanner identifier provided in the certificate matches the scanner identifier retrieved from the ultrasound scanner 110. This act may be performed in a manner similar to act 324 discussed above; except that the approved scanner identifier is compared to the scanner identifier retrieved from the ultrasound scanner 110 at act 206.

Similar to the corresponding acts performed by the scanner 110, the display device 120 may additionally or alternatively control whether the ultrasound scanner is permitted to generate ultrasound image data for display on the multi-use electronic display device 110. For example, this control may be based on whether the display device 120 successfully validates the received digital certificate and/or whether the approved scanner identifier matches the scanner identifier retrieved from the ultrasound scanner 110.

In some embodiments, it is possible to encode permissions data associated with an approved scanner identifier into the digital certificate. For example, permissions data may indicate an operation either or both of the ultrasound scanner and the multi-use electronic display device is capable of performing. In some embodiments, these operations may correspond to the ability of the scanner 110 to perform enhanced software- or firmware-enabled features. For example, in some embodiments, these operations may include enhanced ultrasound imaging modes (e.g., color Doppler) and/or imaging processing algorithms (e.g., automatic calculation of heart rate and/or bladder volume). The encoding of permissions data may be implemented in various ways. For example, in some embodiments, whether certain features are available for a given scanner identifier may be encoded as '1's or '0's in a portion of the certificate to indicate whether a given feature is available. In various embodiments, when encoding the permissions data into a digital certificate at the server 130, the permissions data may be retrieved from the permissions store 138 (as shown in FIG. 1).

If the digital certificate has been encoded with permissions data, act 336 may involve identifying the permissions data for the scanner 110 in the digital certificate. At 338, based on the identified permission data, the display device 120 may restrict operation of certain operations of the scanner 110. For example, if the digital certificate indicates that a color Doppler imaging mode is not permitted to be accessed, the display device 120 may configure the user interface to not allow that feature to be used with the scanner 110.

The encoding of permissions data into the digital certificate (or any other digitally signed communication from a server 130 that needs to be verified by the display device 120) may provide a manufacturer of the scanners 110 with the ability to control the use of features available on the scanner 110. In turn, this may provide flexibility for the manufacturer to create different tiers of feature sets (e.g. 'Basic', 'Premium'), and, for example, ensure that the features intended for the 'Premium' feature are set are not used with the 'Basic' model. While acts 336 and 338 are shown in FIG. 3 as being performed by the display device 120, analogous acts can additionally or alternatively be performed on the ultrasound scanner 110 to effect control of features indicated by the permissions data.

As will be understood by persons skilled in the art, a digital signature may be applied to contents of any message that are themselves encrypted or unencrypted. Thus, the digital certificate discussed above may, in various embodiments, be transmitted in an unencrypted (e.g., plaintext) or an encrypted manner. However, to provide enhanced security, it may be possible to encrypt the digital certificate when the digital certificate is transmitted from the server 130. Then, when the certificate is received, the digital certificate may first be decrypted prior to validation of the digital signature. Since encrypting and decrypting using asymmetric key pairs may be computationally costly, in some embodiments, it may be possible to only encrypt certain sensitive portions of the digital certificate (e.g., the permissions data).

In various embodiments, an attempt to validate a certificate (e.g., acts 320 and/or 330, as discussed above) may additionally or alternatively include checking the status of the certificate. For example, this checking may be to confirm that a given certificate is unexpired and/or unrevoked. While a certificate that is immediately validated after it is received is unlikely to have a status that indicates that it is expired or revoked, a scanner 110 may be configured to attempt re-validating that same certificate at a subsequent point in time to provide enhanced security. For example, re-validation of a certificate may be performed every time a scanner 110 is powered on, and/or periodically after a set amount of time (e.g., every number of days, weeks, or months).

In some embodiments, the checking of the status of a certificate may involve sending a request to determine the status of the certificate. For example, if such a request is sent from the scanner 110, the request may be sent directly to the server 130 or indirectly to the server 130 through the display device 120. If this request is sent from the display device 120, the request may be sent from the display device 120 to the server 130. In various embodiments, this may be performed using a protocol for checking the status of certificates such as the Online Certificate Status Protocol (OCSP). The scanner 110 may, in turn, receive a digitally-signed response to the OCSP request to confirm the status of the certificate. Additionally or alternatively, the scanner 110 may simply receive a new certificate to confirm that the scanner 110 is permitted to operate.

The checking of the status of a certificate as a part of the validation process may allow enhanced control over the operation of a scanner 110 and/or the display device 120. For example, periodic validation of the certificate may provide a mechanism for remotely disabling a scanner 110 by the manufacturer (e.g., as may be desirable if the scanner is stolen or lost). Such feature may be particularly desirable for scanners 110 that are portable and lightweight. Periodic validation of the certificate (including identifying permissions data contained therein) may also allow certain features to be enabled or disabled by the manufacturer. For example, this may be desirable if certain features/operations of the scanner 110 are desired to be enabled for a limited time period (e.g., during a trial usage period).

Part of checking the certificate status may involve determining whether a certificate is expired. In various embodiments, the expiration date of a certificate may be configured according to the desired control of a scanner 110 and/or available operations on the display device 120. For example, in an example scenario where the scanner 110 (or certain features/operations of the scanner 110) is loaned or provided on a trial basis, the certificate may be configured to expire after the trial period expires. This may allow for an automatic disabling of the scanner 110 or features when the trial period ends, such that a user may need to purchase a scanner 110 and/or continue subscribing to certain features/operations to maintain use of the scanner 110 and/or such features. If the purchase is made and/or the subscription continues, the certificate can be renewed or a new certificate issued with a new expiry date.

In some embodiments, the checking of the status of the certificate may not involve sending of a status request to an external device or server 130. Instead, the status determination may simply involve checking whether a given certificate has expired. For example, in this scenario, if a certificate is determined to be unexpired (and one or more of the various validation acts discussed above have been performed successfully), then the certificate may be considered validated so that operation of the scanner 110 and/or any associated features are permitted. However, if the certificate is expired, an external request may need to be performed to renew the certificate and/or retrieve a new certificate with a later expiry date.

Such embodiments may allow a scanner 110 to operate with a display device 120 so long as the certificate is unexpired, and/or the digital signature is validated, and/or the certificate contains the scanner identifier—even in scenarios where there is no Internet connectivity. For example, this may occur if a scanner 110 is used in a remote location (e.g., in a search and rescue operation) or in a disaster response scenario. This may also occur in scenarios where display device 120 typically connects to the Internet via a Wi-Fi™ connection from a base station, but that Internet connection is unavailable because the display device 120 has formed a Wi-Fi Direct™ connection with the scanner 110.

To enable such users to operate a scanner 110, all the necessary certificates for operation may be provisioned to the scanner 110 at the manufacturer. Such certificates can be configured to have lengthy expiry dates relatively far into the future. Scanners provisioned in this manner may not need to retrieve certificates from an external source, and since the certificates are not expired, the scanner 110 may operate with a display device 120 upon a connection being formed between the scanner 110 and the display device 120.

Referring back to FIG. 3, if all the validation discussed above is performed successfully, scanner 110 may proceed to act 340 and the display device 120 may proceed to act 342. Act 340 may allow scanner 110 to receive commands and transmit ultrasound image data, and act 342 may allow the display device 120 to operate the scanner 110 and receive ultrasound image data therefrom.

In various embodiments, the method of FIG. 3 may be performed independently of the method of FIG. 2, or in combination with it. For example, if performed in combination, some or all of acts 312-342 may be performed after 212-230 of FIG. 2 without having to repeat acts 202-210 relating to the display device 120 retrieving the scanner identifier from the scanner 110 and forwarding it to the server 130. When acts of FIG. 3 and FIG. 2 are performed together, such an embodiment may be able to provide enhanced security by providing certificate-level security based on cryptography, and institution affiliation status-level security. As noted above, in one embodiment, including an approved scanner identifier in the digital certificate may be one way the server 130 indicates that a given scanner 110 is affiliated with an institution account, so as to authorize its use by including the approved scanner identifier in the digital certificate sent to the display device 120.

While a number of exemplary aspects and embodiments have been discussed above, those of skill in the art will recognize that there may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

Interpretation of Terms

Unless the context clearly requires otherwise, throughout the description and the
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Unless the context clearly requires otherwise, throughout the description and the claims:
  Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method of controlling operation of an ultrasound scanner by a multi-use electronic display device, the method comprising the multi-use electronic display device performing the steps of:
    determining availability of the ultrasound scanner for connecting to the multi-use electronic display device;
    retrieving a scanner identifier from the ultrasound scanner;
    sending the scanner identifier to a server for determining a digital certificate associated with the ultrasound scanner;
    receiving the digital certificate from the server, wherein the digital certificate comprises an approved scanner identifier and encoded permissions data associated with the approved scanner identifier, the permissions data indicating at least one operation that is performed by the ultrasound scanner and/or the multi-use electronic display device;
    determining whether the digital certificate is valid;
    determining whether the approved scanner identifier matches the scanner identifier retrieved from the ultrasound scanner; and
    controlling whether the ultrasound scanner is permitted to transmit and receive ultrasound energy to generate ultrasound image data for display on the multi-use electronic display device, the controlling being based on whether the multi-use electronic display device successfully validates the digital certificate, and based on whether the approved scanner identifier matches the scanner identifier retrieved from the ultrasound scanner.

2. The method of claim 1, wherein the multi-use electronic display device is provided with a public key, and the determining whether the digital certificate is valid comprises determining whether the digital certificate was digitally signed with a private key corresponding to the public key.

3. The method of claim 1, wherein the method further comprises:
    based on the permissions data, restricting the at least one operation from being performed.

4. The method of claim 1, wherein the at least one operation that is performed by the ultrasound scanner and/or the multi-use electronic display device performs comprises an enhanced ultrasound imaging mode performed by the ultrasound scanner.

5. The method of claim 4, wherein the enhanced ultrasound imaging mode comprises Color Doppler.

6. The method of claim 1, wherein the at least one operation that is performed by the ultrasound scanner and/or the multi-use electronic display device performs comprises an enhanced imaging processing algorithm performed by the multi-use electronic display device.

7. The method of claim 6, wherein the enhanced imaging processing algorithms comprises calculation of heart rate or bladder volume.

8. The method of claim 3, wherein when received from the server, the permissions data encoded in the digital certificate is encrypted, and a remaining portion of the digital certificate is unencrypted, and wherein the permissions data is decrypted prior to restricting the at least one operation from being performed.

9. The method of claim 1, wherein the digital certificate received from the server is encrypted, and the digital certificate is decrypted prior to determining whether the digital certificate is valid.

10. The method of claim 1, wherein upon successfully determining that the digital certificate is valid, the method further comprises:
encrypting communications between the ultrasound scanner and the multi-use electronic display device.

11. The method of claim 1, wherein after a predetermined period of time, the method further comprises re-determining whether the digital certificate is valid, and wherein the re-determining comprising checking a status of the digital certificate.

12. The method of claim 11, wherein when the multi-use display device fails to successfully revalidate the digital certificate, the method further comprises disabling the ultrasound scanner from transmitting and receiving ultrasound energy to generate ultrasound image data for display on the multi-use electronic display device.

13. The method of claim 11, wherein when the multi-use display device fails to successfully revalidate the digital certificate, the method further comprises disabling the at least one operation indicated in the permissions data.

14. The method of claim 11, wherein the checking the status of the digital certificate comprises sending a communication using an Online Certificate Status Protocol (OCSP).

15. The method of claim 11, wherein the checking the status of the digital certificate comprises determining whether the digital certificate is expired, and wherein if the digital certificate is determined to be expired, the method further comprises disabling the ultrasound scanner from transmitting and receiving ultrasound energy to generate ultrasound image data for display on the multi-use electronic display device.

16. The method of claim 15, wherein the digital certificate expiry period is set according to a loan or trial period of the ultrasound scanner.

17. The method of claim 11, wherein the checking the status of the digital certificate comprises determining whether the digital certificate is expired, and wherein prior to an expiry date of the digital certificate, the method further comprises renewing the digital certificate or receiving a new certificate from the server issued with a new expiry date.

18. A multi-use electronic display device comprising one or more processors and a memory storing instructions for execution by the processor, wherein when the instructions are executed by the one or more processors, the multi-use electronic display device is configured to:
determine availability of the ultrasound scanner for connecting to the multi-use electronic display device;
retrieve a scanner identifier from the ultrasound scanner;
send the scanner identifier to a server for determining a digital certificate associated with the ultrasound scanner;
receive the digital certificate from the server, wherein the digital certificate comprises an approved scanner identifier and encoded permissions data associated with the approved scanner identifier, the permissions data indicating at least one operation that is performed by the ultrasound scanner and/or the multi-use electronic display device;
determine whether the digital certificate is valid;
determine whether the approved scanner identifier matches the scanner identifier retrieved from the ultrasound scanner; and
control whether the ultrasound scanner is permitted to transmit and receive ultrasound energy to generate ultrasound image data for display on the multi-use electronic display device, the controlling being based on whether the multi-use electronic display device successfully validates the digital certificate, and based on whether the approved scanner identifier matches the scanner identifier retrieved from the ultrasound scanner.

19. The multi-use electronic display device of claim 18, wherein the processor is further configured to:
based on the permissions data, restrict the at least one operation from being performed.

\* \* \* \* \*

UNITED STATES PATENT AND TRADEMARK OFFICE
CERTIFICATE OF CORRECTION

PATENT NO. : 11,615,178 B2
APPLICATION NO. : 17/209185
DATED : March 28, 2023
INVENTOR(S) : Trevor Stephen Hansen et al.

It is certified that error appears in the above-identified patent and that said Letters Patent is hereby corrected as shown below:

In the Claims

Column 22, Lines 56-60, Claim 4 Should Read:
The method of claim 1 wherein the at least one operation that can be performed by the ultrasound scanner and/or the multi-use electronic display device comprises an enhanced ultrasound imaging mode performed by the ultrasound scanner.

Column 22, Lines 63-67, Claim 6 Should Read:
The method of claim 1 wherein the at least one operation that can be performed by the ultrasound scanner and/or the multi-use electronic display device comprises an enhanced imaging processing algorithm performed by the multi-use electronic display device.

Column 23, Line 1-3, Claim 7 Should Read:
The method of claim 6, wherein the enhanced imaging processing algorithm comprises calculation of heart rate or bladder volume.

Signed and Sealed this
Fourth Day of July, 2023

Katherine Kelly Vidal
*Director of the United States Patent and Trademark Office*